US012767569B2

(12) United States Patent
Kang et al.

(10) Patent No.: US 12,767,569 B2
(45) Date of Patent: Oct. 20, 2026

(54) RESOURCE-CIRCULATION-TYPE AND ECO-FRIENDLY LIVESTOCK MANURE TREATMENT METHOD USING ALGAL BIOMASS, AND SYSTEM FOR PRODUCING ALGAL BIOMASS USED THEREIN

(71) Applicant: Korea Institute of Ocean Science & Technology, Busan (KR)

(72) Inventors: Do-Hyung Kang, Jeju-si (KR); Yong-Kyun Ryu, Jeju-si (KR); Won-Kyu Lee, Jeju-si (KR); Woon-Yong Choi, Jeju-si (KR); Tae-Ho Kim, Jeju-si (KR); Yeon-Ji Lee, Jeju-si (KR); Areumi Park, Jeju-si (KR); Youn Sik Jeong, Jeju-si (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 430 days.

(21) Appl. No.: 18/551,130

(22) PCT Filed: Apr. 1, 2022

(86) PCT No.: PCT/KR2022/004743
§ 371 (c)(1),
(2) Date: Sep. 18, 2023

(87) PCT Pub. No.: WO2022/244974
PCT Pub. Date: Nov. 24, 2022

(65) Prior Publication Data

US 2024/0158273 A1 May 16, 2024

(30) Foreign Application Priority Data

May 18, 2021 (KR) ........................ 10-2021-0063786

(51) Int. Cl.
*C02F 3/32* (2023.01)
*A01G 33/00* (2006.01)
(Continued)

(52) U.S. Cl.
CPC .............. *C02F 3/322* (2013.01); *A01G 33/00* (2013.01); *A23K 10/30* (2016.05); *C02F 3/32* (2013.01);
(Continued)

(58) Field of Classification Search
CPC .... C02F 3/322; C02F 3/32; C02F 9/00; C02F 2101/105; C02F 2101/16; C02F 2103/20;
(Continued)

(56) References Cited

U.S. PATENT DOCUMENTS

2019/0241847 A1* 8/2019 Krivov .................. C12M 33/00

FOREIGN PATENT DOCUMENTS

CN 1715210 A 1/2006
CN 102946738 B * 4/2015 ............ A23L 17/60
(Continued)

OTHER PUBLICATIONS

Machine-generated English translation of JP 2003-88838, generated on Dec. 20, 2025.*
(Continued)

*Primary Examiner* — Fred Prince
(74) *Attorney, Agent, or Firm* — WOMBLE BOND DICKINSON (US) LLP

(57) ABSTRACT

The present disclosure provides a resource-circulation-type and eco-friendly livestock manure treatment method, and a system for producing algal biomass used therein, the method being capable of: preventing water pollution while allowing livestock liquid fertilizer to be treated on the basis of a
(Continued)

biological process; producing algal biomass; and supplying the produced algal biomass to livestock feed and farms.

20 Claims, 7 Drawing Sheets

(51) Int. Cl.

| | |
|---|---|
| ***A23K 10/30*** | (2016.01) |
| ***C02F 9/00*** | (2023.01) |
| ***C05F 3/00*** | (2006.01) |
| ***C12M 1/00*** | (2006.01) |
| ***C12M 1/06*** | (2006.01) |
| ***C12M 1/34*** | (2006.01) |
| ***C12N 1/12*** | (2026.01) |
| ***C12N 1/125*** | (2026.01) |
| *C02F 101/10* | (2006.01) |
| *C02F 101/16* | (2006.01) |
| *C02F 103/20* | (2006.01) |
| *C12R 1/89* | (2006.01) |

(52) U.S. Cl.

CPC .................. *C02F 9/00* (2013.01); *C05F 3/00* (2013.01); *C12M 1/00* (2013.01); *C12M 1/06* (2013.01); *C12M 1/34* (2013.01); *C12N 1/12* (2013.01); *C12N 1/125* (2021.05); *C02F 2101/105* (2013.01); *C02F 2101/16* (2013.01); *C02F 2103/20* (2013.01); *C02F 2203/006* (2013.01); *C12R 2001/89* (2021.05); *Y02E 50/30* (2013.01); *Y02W 30/40* (2015.05)

(58) Field of Classification Search

CPC ... C02F 2203/006; A01G 33/00; A23K 10/30; C05F 3/00; C12M 1/00; C12M 1/06; C12M 1/34; C12N 1/12; C12N 1/125; C12R 2001/89; Y02E 50/30; Y02W 30/40

USPC ......................... 210/602, 612, 903, 906, 908

See application file for complete search history.

(56) References Cited

FOREIGN PATENT DOCUMENTS

| | | | | | |
|---|---|---|---|---|---|
| CN | 105621794 | A | | 6/2016 | |
| CN | 106867890 | A | * | 6/2017 | ............ C12M 41/26 |
| CN | 109504609 | A | | 3/2019 | |
| FR | 3041654 | A1 | * | 3/2017 | ............... C12N 1/12 |
| JP | 2003-88838 | A | | 3/2003 | |
| KR | 10-0723338 | B1 | | 5/2007 | |
| KR | 10-0949314 | B1 | | 3/2010 | |
| KR | 10-0966279 | B1 | | 6/2010 | |
| KR | 10-2014-0027793 | A | | 3/2014 | |
| KR | 10-2016-0057344 | A | | 5/2016 | |
| KR | 10-2018-0010296 | A | | 1/2018 | |
| KR | 10-2018-0105454 | A | | 9/2018 | |
| KR | 10-2019-0053400 | A | | 5/2019 | |

OTHER PUBLICATIONS

Machine-generated English translation of KR 20160057344, generated on Dec. 20, 2025.*

Machine-generated English translation of FR 3041654, generated on Dec. 20, 2025.*

Machine-generated English translation of CN 106867890, generated on Dec. 20, 2025.*

Machine-generated English translation of CN 102946738, generated on Dec. 20, 2025.*

Machine-generated English translation of KR 20180010296, generated on Dec. 20, 2025.*

First Office Action for Chinese Patent Application No. 202280024149.6, dated Jun. 19, 2025, 8 pages and English translation, 8 pages.

International Search Report of PCT/KR2022/004743, Jul. 25, 2022, 5 pages.

Office Action for Chinese Patent Application No. 202280024149.6, dated Apr. 17, 2026, 9 pages and English translation, 9 pages.

* cited by examiner

[FIG. 1]
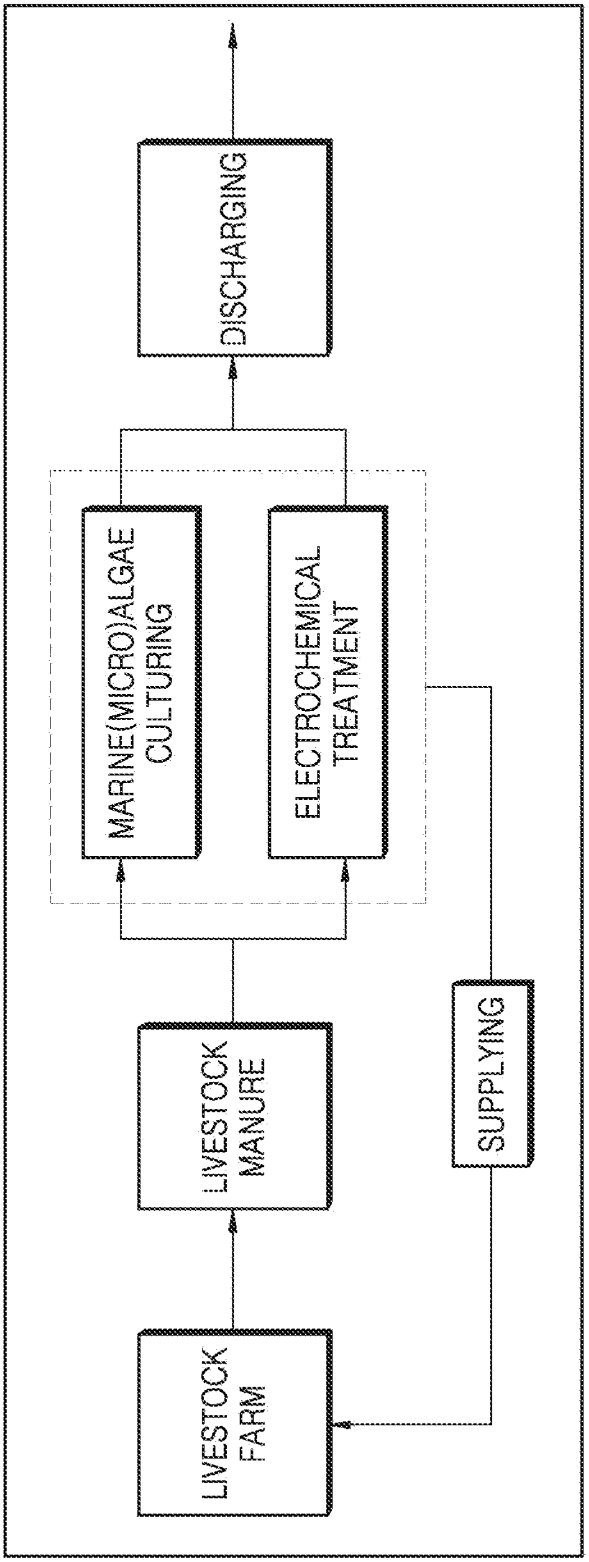

[FIG. 2]
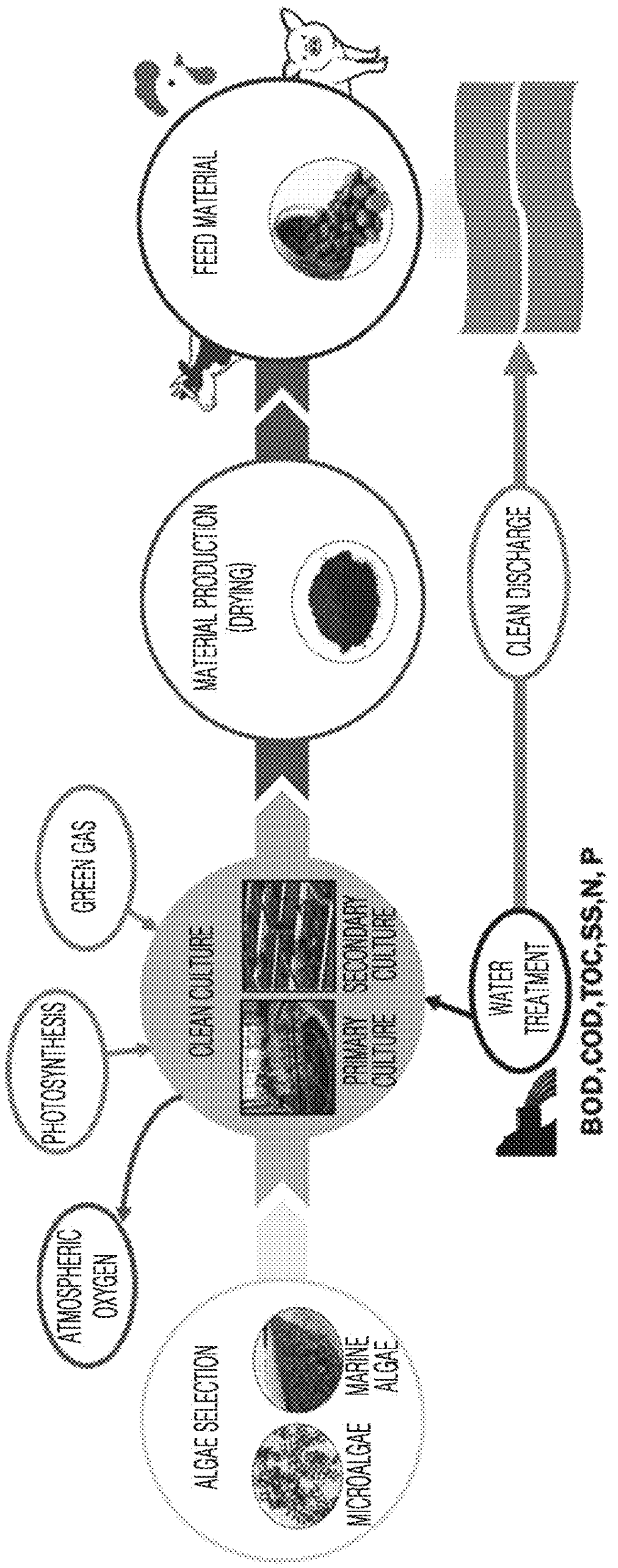

[FIG. 3]
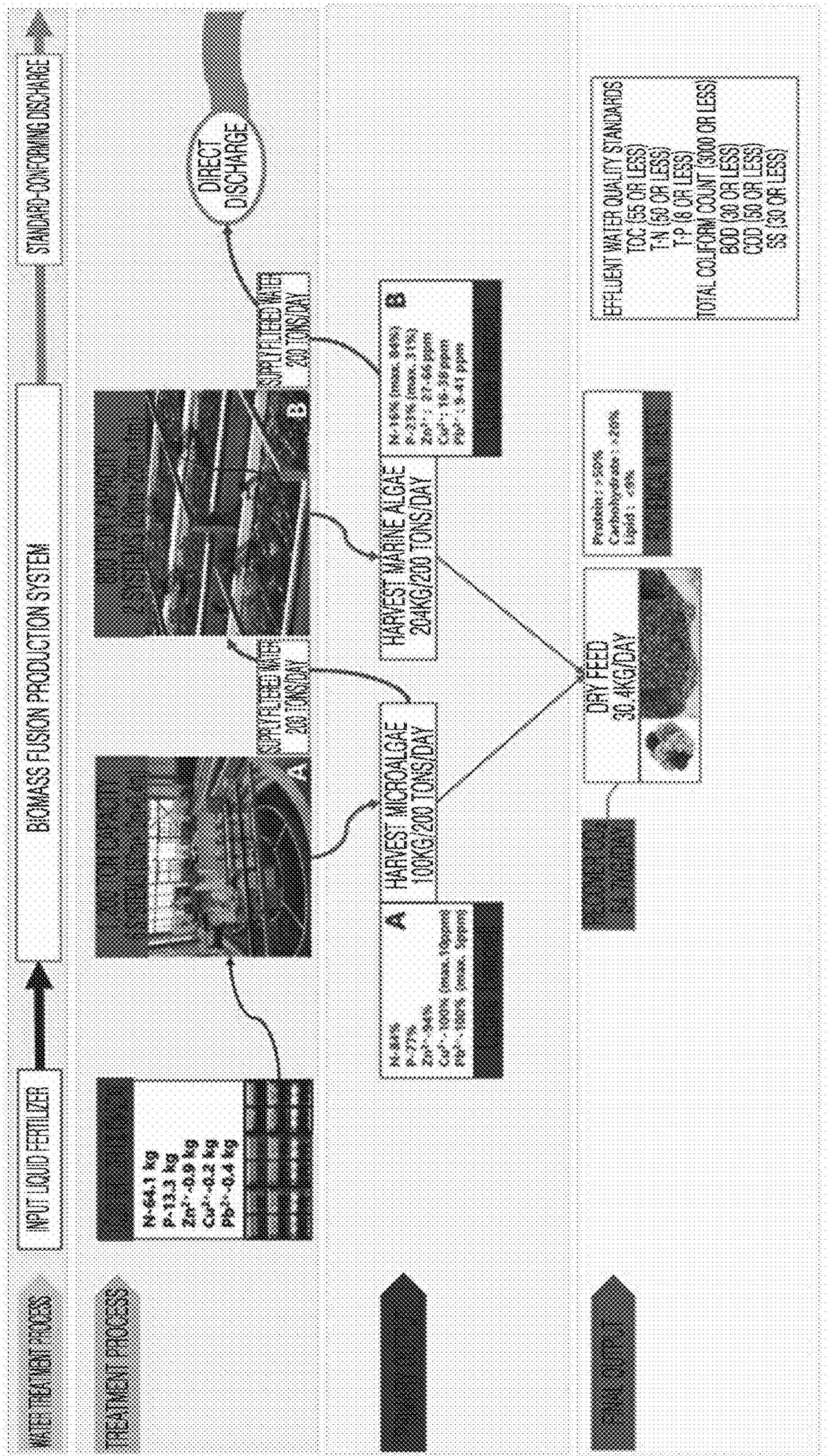

[FIG. 4]
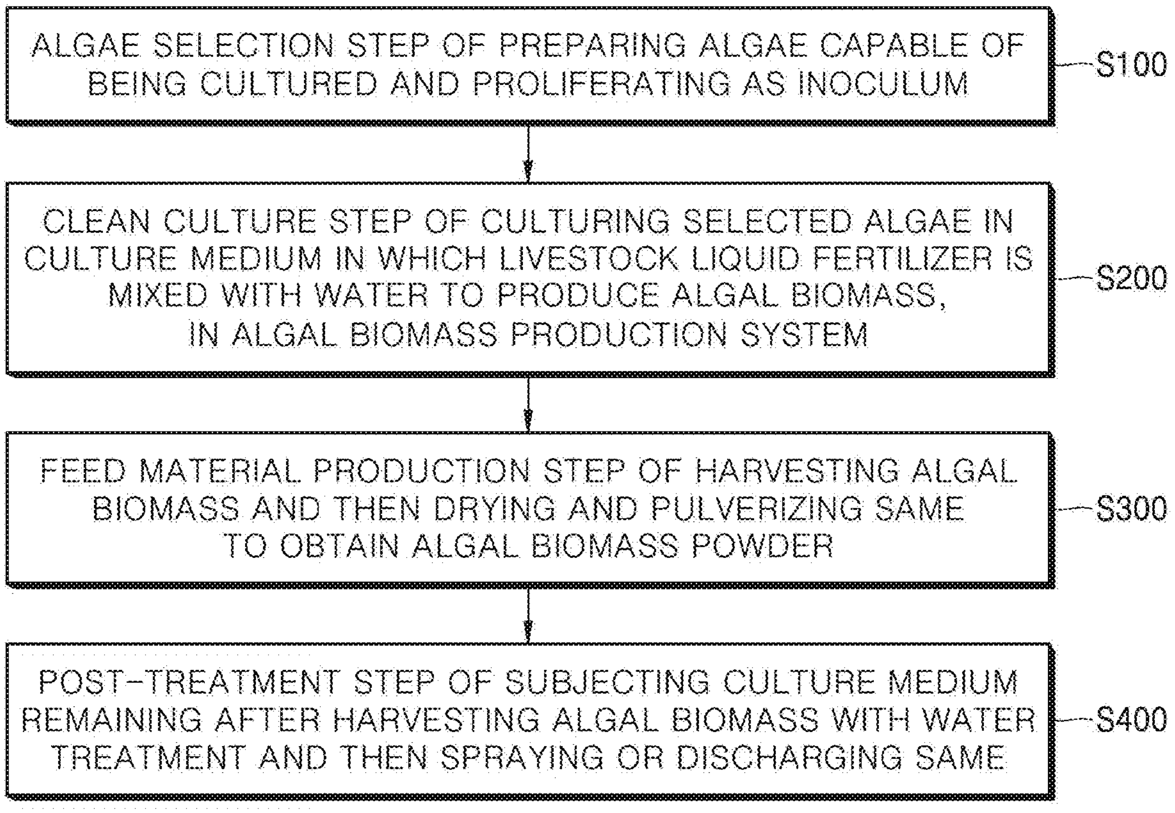

[FIG. 5]
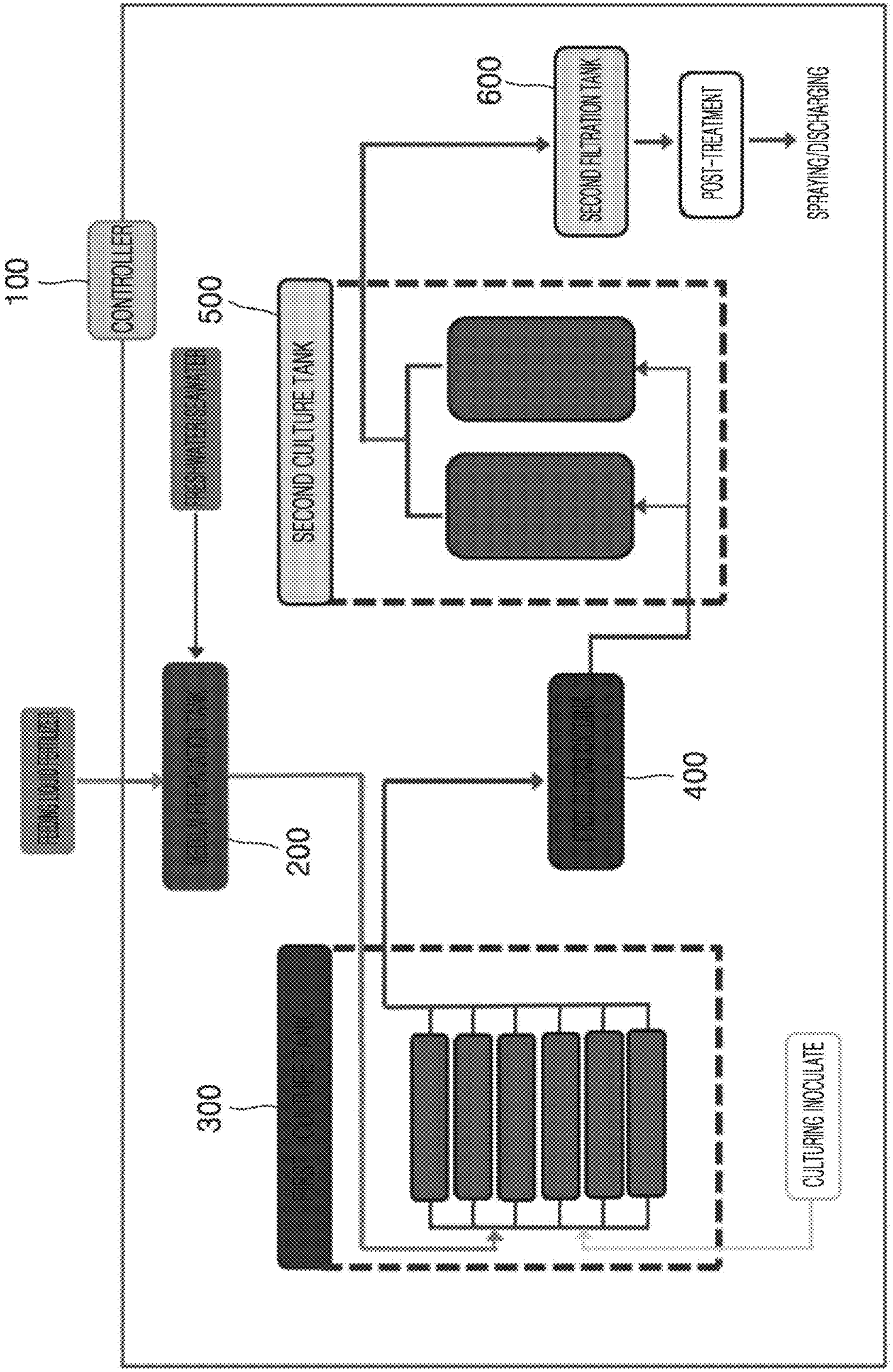

[FIG. 6]
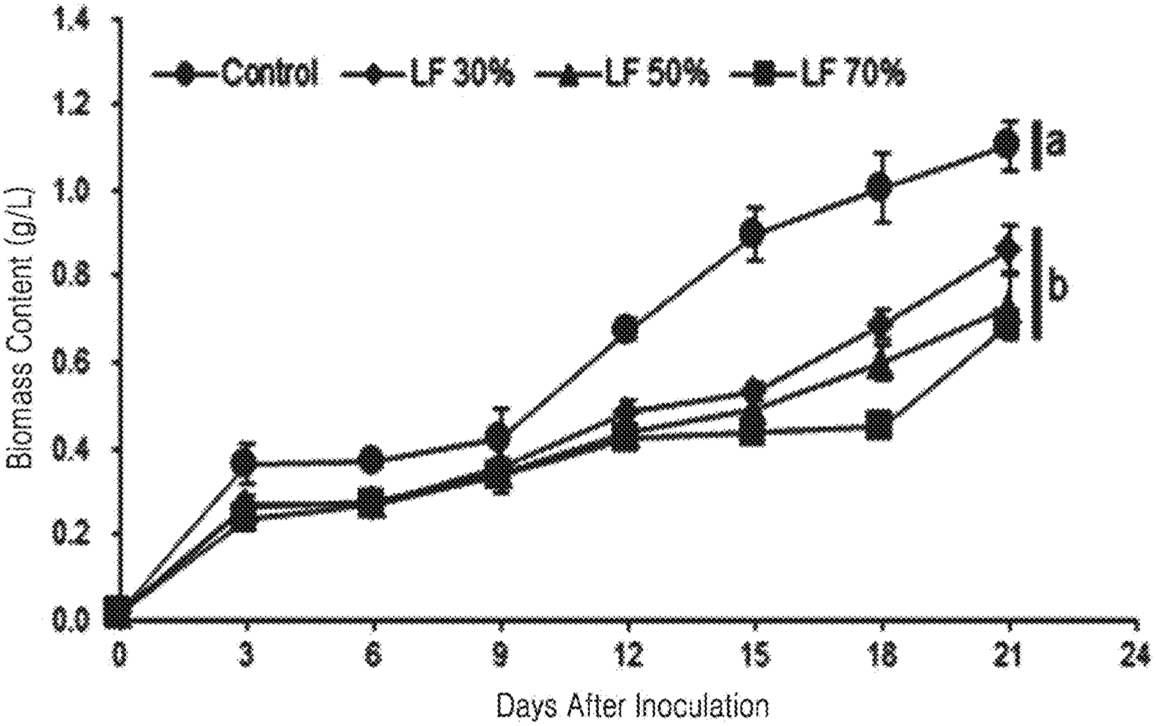
[FIG. 7]
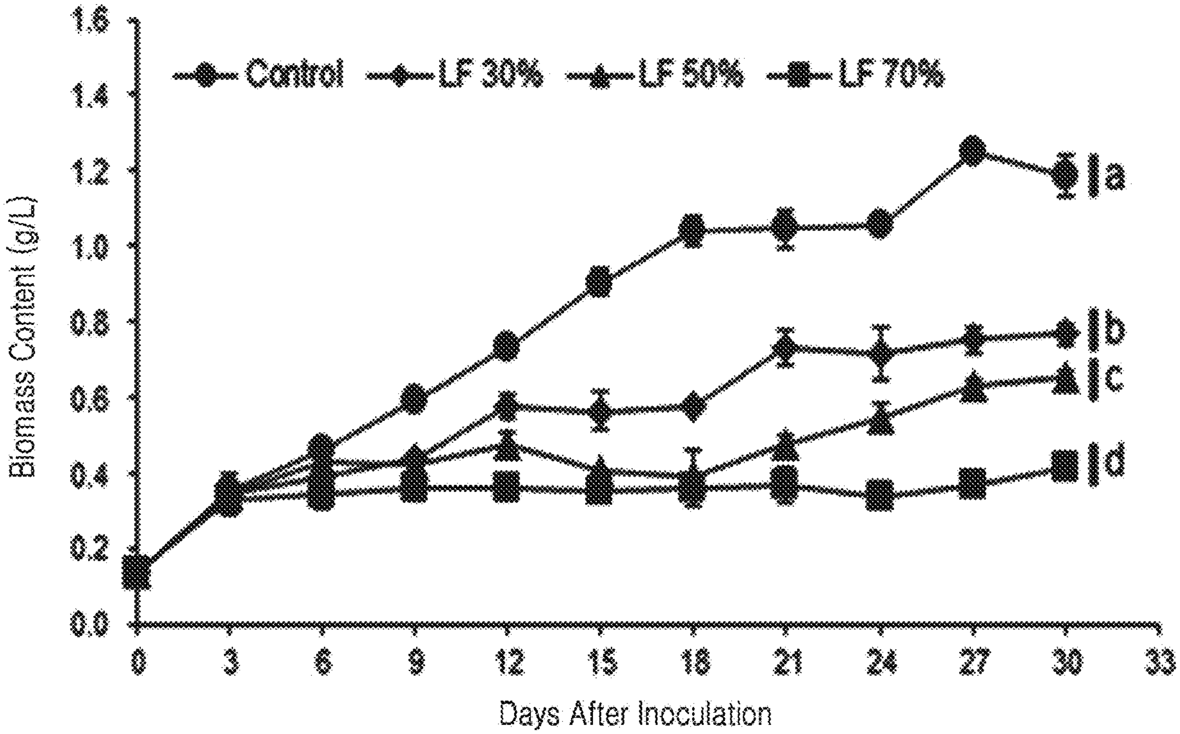

[FIG. 8]
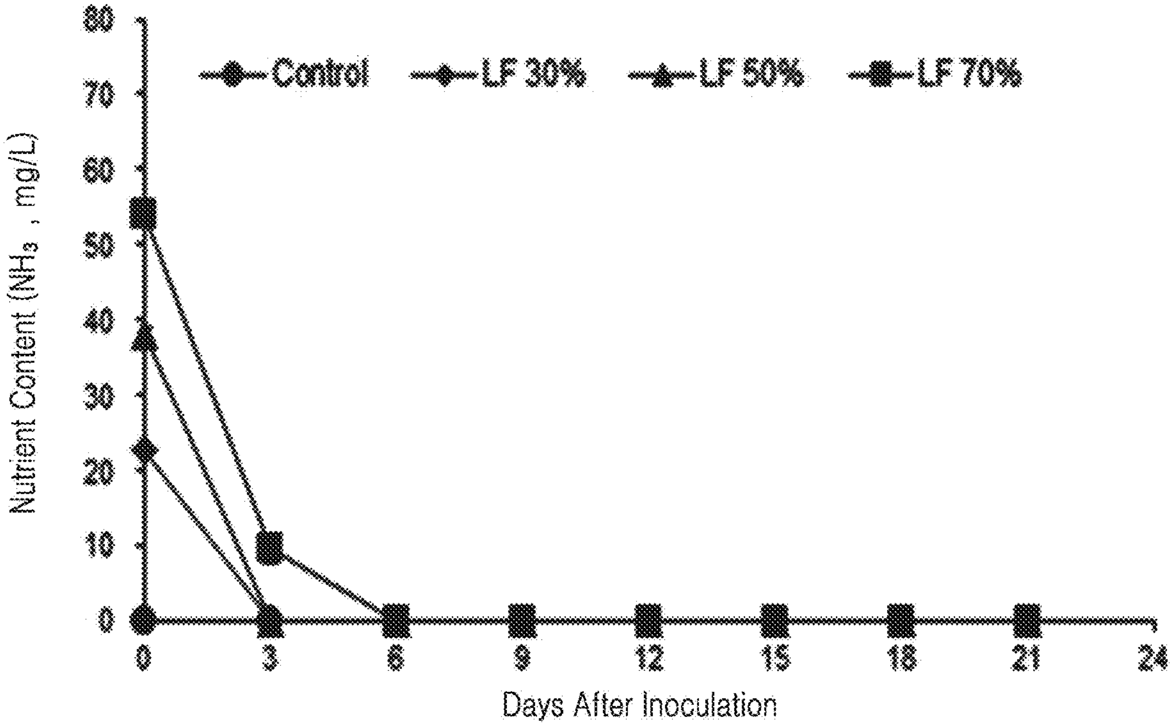
[FIG. 9]
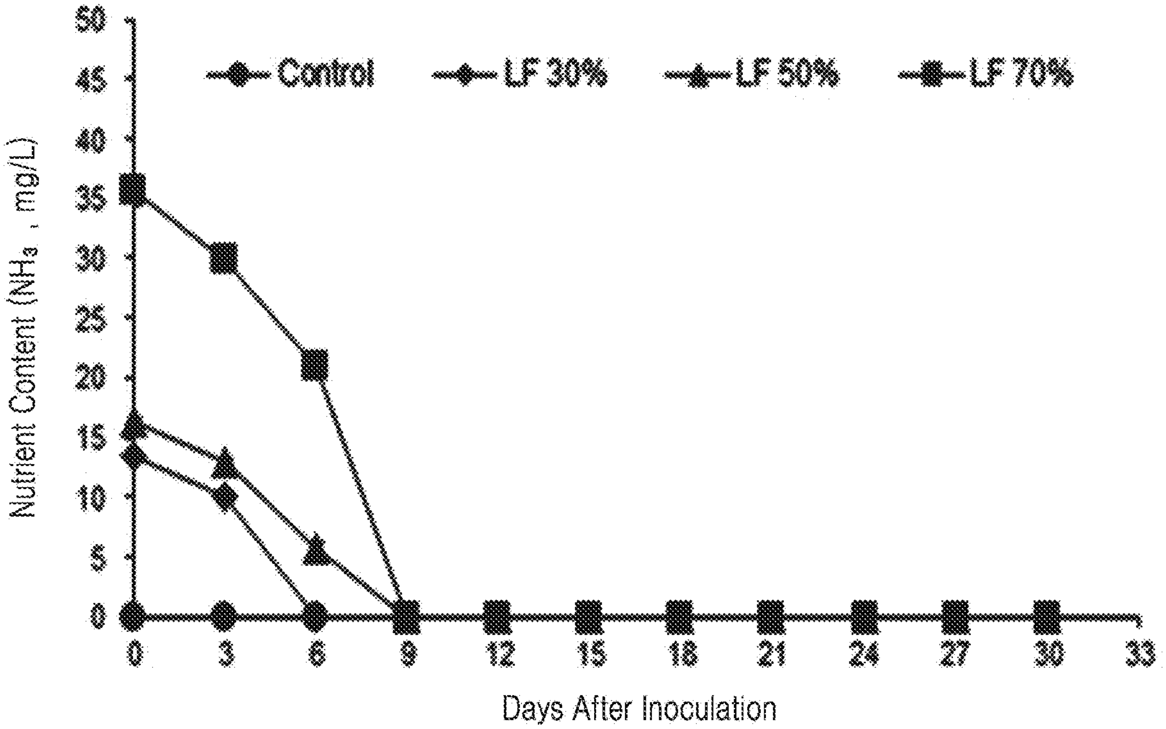

RESOURCE-CIRCULATION-TYPE AND ECO-FRIENDLY LIVESTOCK MANURE TREATMENT METHOD USING ALGAL BIOMASS, AND SYSTEM FOR PRODUCING ALGAL BIOMASS USED THEREIN

CROSS-REFERENCE TO RELATED APPLICATION

This application is a U.S. National Phase Patent Application of International Application Number PCT/KR2022/004743, filed on Apr. 1, 2022, which claims priority of Korean Patent Application Number 10-2021-0063786, filed on May 18, 2021, the entire content of each of which is incorporated herein by reference.

TECHNICAL FIELD

The present disclosure relates to a resource-circulation-type and eco-friendly livestock manure treatment method using algal biomass, and a system for producing algal biomass used therein. In more detail, the present disclosure relates to a resource-circulation-type and eco-friendly livestock manure treatment method, and a system for producing algal biomass used therein, the method being capable of: preventing water pollution while allowing livestock liquid fertilizer to be treated on the basis of a biological process; producing algal biomass; and supplying the produced algal biomass to livestock feed and farms.

BACKGROUND ART

Livestock manure generally refers to manure discharged from livestock such as cows, pigs, and chickens. Currently, the most common treatment process is microbial fermentation, and generated methane gas is recovered as an energy resource through a biogasification process. On the other hand, solids are separated into compost solidified through dewatering process and liquid fertilizer discharged through filtration and spread to farmland, reclaimed land, and forest fields.

Bio-gasification has the principle of decomposing manure in an aerobic digestion tank to generate methane gas, and generating electricity by using the methane gas produced in such way as a raw material for a cogeneration generator. The electricity generated in the cogeneration process can be sold to the national electric power corporation or supplied to nearby farmlands, and the generated waste heat can be used for heating the building. Further, additionally generated organic matter can be reused as fertilizer.

In general, livestock manure composting is that, livestock manure is decomposed by aerobic microorganisms under the condition that air is supplied, and, as a result, it is converted into nutrients such as nitrogen, phosphorus, and potassium and various trace nutrients. In order to successfully perform composting, it is very important to control the moisture content (largely 70-80%) and the air content (150 l/min·1 $m^3$) in the compost. The moisture content of the manure for each livestock is different. In the case of pigs, the moisture content is high, so it is important to control it through a generalized process.

The liquid fertilizer produced together with solids through a solid-liquid separator is primarily collected in a liquid manure storage tank. The liquid fertilizer is fermented and aged through the processes of the first low-aeration period, second and third over-aeration period, and fourth low-aeration period fermentation tanks, and is loaded onto a transport vehicle to be sprayed.

The liquid fertilizer treated with the conventional techniques in the art contains up to 4,200 mg/kg of ammonia nitrogen, and the Cu and Zn concentrations of the soil in the liquefied manure application area reach 260 and 1,500 mg/kg, respectively, due to feed additives, resulting in secondary cause contamination problems. In some areas, groundwater wells may exceed the nitrate nitrogen environmental standard (10 mg/kg) due to liquid fertilization and increased use of chemical fertilizers.

Most of the solid compost and liquid fertilizer are treated according to the standards of the Ministry of Environment, and are transferred to farmland, forest and reclaimed land and spread. In particular, nutrient salts such as nitrate and phosphate and heavy metals may cause soil acidification and contamination, and liquid fertilizers may affect contamination of groundwater as well as soil, so they must be discharged according to strict standards.

However, there are frequent cases in which some individual livestock sheds discharge liquid fertilizers into soil or rivers that do not meet the discharge standards of the Ministry of Environment, causing serious environmental pollution. In addition, in contrast to the continuous productivity of livestock manure, the period of spreading solid compost and liquid fertilizer to be treated is limited. Thus, it is also a matter to be improved in the existing process that time and space discrepancy between manure generation and treatment occurs.

In addition, the process according to the conventional techniques in the art passes through several steps and, thus, is very complicated, and requires an expensive cost for facility construction and operation, so the development of a more economical process is urgently required.

DISCLOSURE

Technical Problem

In order to solve the above-mentioned problems of the conventional techniques in the art, the present inventors found out a paradigm of an eco-friendly liquid manure resource circulation structure that can minimize environmental damage due to temporal and spatial inconsistency in the production and treatment of livestock manure, and understood that it is necessary to develop new livestock manure utilization technology that can fundamentally prevent contamination of underground water and rivers by optimizing the concentration of organic matter, nitrogen, phosphorus, and heavy metals with high pollution load among the components of livestock manure based on the final discharge water standard. Therefore, they completed the present disclosure.

Accordingly, an objective of the present disclosure is to provide a resource-circulation-type and eco-friendly livestock manure treatment method capable of: preventing water pollution while allowing livestock liquid fertilizer to be treated on the basis of a biological process; producing algal biomass; and supplying the produced algal biomass to livestock feed and farms.

Another objective of the present disclosure is to provide an algal biomass production system for producing algal biomass.

Another objective of the present disclosure is to provide use of the produced algal biomass.

Technical Solution

In order to achieve the above-mentioned objectives, as a first embodiment of the present disclosure, there is provided a resource-circulation-type and eco-friendly livestock manure treatment method comprising the steps of (a) an algae selection step of preparing algae capable of being cultured and proliferating as inoculum; (b) a clean culture step of culturing the selected algae in a culture medium in which a livestock liquid fertilizer is mixed with water to produce algal biomass, in an algal biomass production system; (c) a feed material production step of harvesting the algal biomass, followed by drying and pulverizing to obtain algal biomass powder; and (d) a post-treatment step of subjecting the culture medium remaining after harvesting the algal biomass in the clean culture step with water treatment, followed by spraying or discharging.

In addition, the present disclosure provides a resource-circulation-type and eco-friendly livestock manure treatment method using algal biomass, wherein the algae is at least one selected from the group consisting of microalgae and marine algae.

In addition, the present disclosure provides a resource-circulation-type and eco-friendly livestock manure treatment method using algal biomass, wherein the microalgae comprises at least one selected from the group consisting of *Spirulina* sp., *Chlorella* sp., *Scenedesmus* sp., *Chlorococcum* sp., *Chlamydomonas* sp., *Microcystis* sp. and *Euglena* sp.

In addition, the present disclosure wherein provides a resource-circulation-type and eco-friendly livestock manure treatment method using algal biomass, wherein the marine algae comprises at least one selected from the group consisting of *Enteromorpha* sp., *Ulva* sp., *Saccharina* sp., *Garcilaria* sp. and *Sargassum* sp.

In addition, the present disclosure wherein provides a resource-circulation-type and eco-friendly livestock manure treatment method using algal biomass, wherein the algal biomass production system comprises a controller for controlling the culture environment; a medium preparation tank for preparing a culture medium for culturing microalgae or marine algae; a first culture tank for culturing microalgae by introducing the culture medium and microalgae as inoculum into; a first filtration tank for filtering the microalgae and culture medium cultured in the first culture tank; a second culture tank for culturing marine algae by introducing marine algae into the culture medium and inoculum obtained from the first filtration tank; and a second filtration tank for filtering the marine algae and culture medium cultured in the second culture tank.

In addition, the present disclosure wherein provides a resource-circulation-type and eco-friendly livestock manure treatment method using algal biomass, wherein in the culture medium of step (b), the liquid fertilizer and water are mixed in a volume ratio of 1:9 to 9:1.

In addition, the present disclosure wherein provides a resource-circulation-type and eco-friendly livestock manure treatment method using algal biomass, wherein the first culture tank and the second culture tank further comprise at least one of a raceway pond and a photo-bioreactor; an agitator of at least one of a screw type, a paddle type, a propeller type and a water wheel type; and a heating device and a cooling device for maintaining the optimal culture temperature in the culture tank.

In addition, the present disclosure wherein provides a resource-circulation-type and eco-friendly livestock manure treatment method using algal biomass, wherein the harvesting of the algal biomass is performed by at least one of filtration, sedimentation, flotation, centrifugation and flocculation.

In addition, the present disclosure wherein provides a resource-circulation-type and eco-friendly livestock manure treatment method using algal biomass, wherein the drying is performed by at least one of freeze drying, far-infrared ray drying, vacuum drying, hot air drying, spray drying, drum drying and natural drying.

In addition, the present disclosure wherein provides a resource-circulation-type and eco-friendly livestock manure treatment method using algal biomass, wherein the water treatment is performed to meet the effluent water quality standards of Biological Oxygen Demand (BOD, mg/L) of 30 or less; Chemical Oxygen Demand (COD, mg/L) of 50 or less; Total Organic Carbon (TOC, mg/L) of 3000 or less; Total Nitrogen (T-N, mg/L) of 60 or less; Total phosphorus (T-P, mg/L) of 8 or less; Suspended matter amount (SS, mg/L) of 30 or less; and Total Coliform Count (number/mL) of less than 3000.

In order to achieve the above-mentioned objectives, as a second embodiment of the present disclosure, there is provided an algal biomass production system for treating resource-circulation-type livestock manure using algal biomass, wherein the system comprises a controller for controlling the culture environment; a medium preparation tank for preparing a culture medium for culturing microalgae or marine algae; a first culture tank for culturing microalgae by introducing the culture medium and microalgae as inoculum into; a first filtration tank for filtering the microalgae and culture medium cultured in the first culture tank; a second culture tank for culturing marine algae by introducing the culture medium obtained from the first filtration tank and marine algae as inoculum into; and a second filtration tank for filtering the marine algae and culture medium cultured in the second culture tank.

In addition, the present disclosure provides an algal biomass production system for treating resource-circulation-type livestock manure using algal biomass, wherein the first culture tank and the second culture tank further comprise at least one of a raceway pond and a photo-bioreactor.

In addition, the present disclosure provides an algal biomass production system for treating resource-circulation-type livestock manure using algal biomass, wherein the first culture tank and the second culture tank further comprise an agitator of at least one of a screw type, a paddle type, a propeller type and a water wheel type.

In addition, the present disclosure provides an algal biomass production system for treating resource-circulation-type livestock manure using algal biomass, wherein the first culture tank and the second culture tank further comprise a heating device and a cooling device for maintaining the optimal culture temperature in the culture tank.

In order to achieve the above-mentioned objectives, as a third embodiment of the present disclosure, there is provided an animal feed material containing algal biomass powder obtained by the resource-circulation-type and eco-friendly livestock manure treatment method using algal biomass according to the first embodiment.

In addition, the present disclosure provides an animal feed material in which the animal feed material is used as a raw material for feed additives or feed compositions.

Advantageous Effects

According to the present disclosure, the environmental problems of the conventional techniques in the art are overcome and an eco-friendly resource virtuous cycle of livestock liquid fertilizer is possible.

That is, the resource-circulation-type eco-friendly livestock manure treatment method and algal biomass production system using algal biomass of the present disclosure have the advantages that it can select species according to the salt concentration of 3000 to 15,000 ppm to culture marine biomass, and control the composition of the culture medium through the operation of a combination of seawater (concentrated water)/liquid fertilizer.

In addition, when using a liquid fertilizer of 50 $m^3$/d, the method and system of the present disclosure have the advantage that it can stably produce about 250 kg (based on wet *Spirulina*)/d while digesting most of the nutrients in the liquid fertilizer.

In addition, culturing marine biomass enables the treatment of nutrients and the cultivation of microalgae/marine algae. In addition, the produced microalgae and marine algae can be supplied again as feed for livestock. Therefore, the method and system of the present disclosure have the advantage that a virtuous cycle of resource utilization of livestock manure is possible.

Finally, the resource-circulation-type and eco-friendly livestock manure treatment method using algae biomass according to the present disclosure has the advantage that the final discharged water can be discharged so that the water quality meets the existing sewage effluent water quality standards.

DESCRIPTION OF DRAWINGS

FIG. 1 is a process chart of eco-friendly resource recycling and treatment technology of livestock manure using algae biomass according to the present disclosure.

FIG. 2 is a conceptual diagram showing a resource-circulation-type and eco-friendly livestock manure treatment method using algae biomass according to the present disclosure.

FIG. 3 is a conceptual diagram of empirical research digitization showing a resource-circulation-type and eco-friendly livestock manure treatment method using algae biomass according to the present disclosure.

FIG. 4 shows a flow chart of a resource-circulation-type and eco-friendly livestock manure treatment method using algae biomass according to an embodiment of the present disclosure.

FIG. 5 shows an algal biomass production system for treating resource-circulation-type and eco-friendly livestock manure using algae biomass according to an embodiment of the present disclosure.

FIG. 6 is a graph showing changes in biomass productivity over time in 1 L culture experiment results according to an embodiment of the present disclosure.

FIG. 7 is a graph showing changes in biomass productivity over time in 200 L culture experiment results according to an embodiment of the present disclosure.

FIG. 8 is a graph showing changes in ammonia absorption over time in 1 L culture experiment results according to an embodiment of the present disclosure.

FIG. 9 is a graph showing changes in ammonia absorption over time in 200 L culture experiment results according to an embodiment of the present disclosure.

BEST MODE

It should be noted that in the following description, only parts necessary for understanding the embodiments of the present disclosure are described, and descriptions of other parts will be omitted without disturbing the gist of the present disclosure.

Terms or words used in the present specification and claims described below should not be construed as being limited to ordinary or dictionary meanings and should be interpreted as meanings and concepts consistent with the technical spirit of the present disclosure based on the principle that the inventor may appropriately define a concept of terms in order to best describe his/her invention.

Therefore, the embodiments described in this specification and the features shown in the drawings are only preferred embodiments of the present disclosure, and do not represent all of the technical idea of the present disclosure. Therefore, it should be understood that there may be various equivalents and modifications that can replace them at the time of filing of the present disclosure.

In the present disclosure, "livestock manure" or "livestock manure" refers to feces and urine excreted by livestock, and feces and urine mixed with water used in the course of using livestock.

In the present disclosure, "livestock" refers to cattle, pigs, horses, chickens, and other breeding animals.

In the present disclosure, "compost" refers to materials other than liquid fertilizer among materials containing fertilizer components made by fermenting livestock manure.

In the present disclosure, "liquid fertilizer" refers to a material containing fertilizer components made by preprocessing livestock manure and fermenting it in a liquid state.

Membrane treatment techniques such as multi-layer filtration (MMF), microfiltration (MF), and ultrafiltration (UF) may be applied to the pretreatment in order to remove suspended matter in livestock manure, but the present disclosure is not limited thereto.

In addition, ozone microbubble Advanced Oxidation Process (AOP) may be additionally applied to the pretreatment in order to remove BOD, color, turbidity, *E. coli*, etc. of livestock manure and treat non-degradable pollutants, but the present disclosure is not limited thereto.

Since nutrients contained in the pretreated liquid fertilizer must be electrochemically converted into gas, a reverse electrodialysis-type salt gradient power generation technology may be applied as the electrochemical treatment method, but the present disclosure is not limited thereto.

Hereinafter, a preferred embodiment according to the present disclosure is described in detail with reference to the accompanying drawings, but if it is determined that the detailed description of related known technologies for describing the present disclosure may obscure the gist of the present disclosure, the detailed description is omitted.

FIG. 1 is a process chart of eco-friendly resource recycling and treatment technology of livestock manure using algae biomass according to the present disclosure. The specific process of the present technology may comprise the following steps: a producing step of livestock manure discharged from livestock farms; a marine (microalgae) algae culturing step of environmentally friendly processing of the liquid fertilizer pretreated from the produced livestock manure by applying a biological treatment technology based on an algal biomass system; an electrochemical treatment step of converting nutrients into gas form while producing electrical energy using additionally pretreated liquid fertilizer to optimize resource recycling from livestock manure; and a step of supplying the produced resources as feed for livestock farms and barns, and spraying and discharging the final discharged water, but the present disclosure is not limited thereto.

FIG. 2 is a conceptual diagram showing a resource-circulation-type and eco-friendly livestock manure treatment method using algae biomass according to the present disclosure.

Referring to FIG. 2, The algal biomass production system of the resource-circulation-type and eco-friendly livestock manure treatment method using algae biomass according to the present disclosure should be installed near a livestock manure treatment facility where liquid fertilizer is easily supplied to efficiently culture algae. The biomass convergence production system installed near the livestock manure treatment facility can sequentially perform the processes of bird selection, clean culture, material production (drying) and materialization of feed.

In addition, the system according to the present disclosure has a multi-purpose virtuous cycle structure that, through the above-mentioned process, carbon dioxide, a greenhouse gas, may be converted into oxygen through photosynthesis and discharged into the atmosphere, and the final algae biomass harvest may be used as feed, and purified livestock liquid fertilizer may be discharged cleanly into rivers or lakes or spread on farmland.

It is essential to purify the liquid manure and select species capable of being cultured and propagating in the process of selecting microalgae and marine algae suitable in the resource-circulation-type and eco-friendly livestock manure treatment method using algae biomass according to an embodiment of the present disclosure.

The microalgae, for example, comprises *Spirulina* sp., *Chlorella* sp., *Scenedesmus* sp., *Chlorococcum* sp., *Chlamydomonas* sp., *Microcystis* sp., *Euglena* sp., and so on, but the present disclosure is not limited thereto.

The marine algae, for example, comprises *Enteromorpha* sp., *Ulva* sp., *Saccharina* sp., *Garcilaria* sp., *Sargassum* sp., and so on, but the present disclosure is not limited thereto.

It is preferable to select the microalgae of the present disclosure, culture the selected microalgae at a constant temperature and culture conditions and grow them for 7 to 14 days, and then inoculate the inoculum of about 1% of the total amount of a culture composition to the culture composition containing the livestock liquid fertilizer.

In the clean culture process of the resource-circulation-type and eco-friendly livestock manure treatment method using algae biomass according to an embodiment of the present disclosure, microalgae and marine algae are sequentially cultured in a culture medium and harvested, thereby producing algae biomass and purifying excess nutrients in the liquid manure.

In the material production (drying) process of the resource-circulation-type and eco-friendly livestock manure treatment method using algal biomass according to an embodiment of the present disclosure, the harvested algal biomass may be prepared in powder form by various drying methods.

The drying method used at this time comprises freeze drying, far infrared drying, vacuum drying, hot air drying, spray drying, drum drying and natural drying, and algal biomass that has been dried may be prepared in the form of a fine powder using a grinding process.

In the feed materialization process of the resource-circulation-type and eco-friendly livestock manure treatment method using algal biomass according to an embodiment of the present disclosure, the dried algae powder may be extracted and processed to be materialized into livestock feed additives and feed.

In addition, the algae grows by taking as nutrients various nutrients that are present in large amounts in the livestock liquid fertilizer and, thus, may be used as an effective purification means. Therefore, after harvesting the algae, the culture composition containing the livestock liquid fertilizer may undergo a post-treatment process and be sprayed and discharged to the outside after inspecting whether the water meets the effluent water quality standards.

FIG. 3 a conceptual diagram of empirical research digitization showing a resource-circulation-type and eco-friendly livestock manure treatment method using algae biomass according to the present disclosure, and roughly quantifies the supply and output in the process step and the scale of the process step of the biomass convergence production system according to an embodiment of the present disclosure based on previous research data.

The water treatment process is largely classified into a liquefied fertilizer input step, a biomass fusion production step, and a standard-compliant discharge step, and is performed sequentially. When 100 ton/day of liquid fertilizer is produced, the components of liquid fertilizer comprise nutrients and heavy metals of 64.1 kg of N, 13.3 kg of P, 0.9 kg of $Zn^{2+}$, 0.2 kg of $Cu^{2+}$, and 0.4 kg of $Pb^{2+}$.

The liquid fertilizer is used as a culture medium firstly in 6 microalgae incubators (50 m*10 m*0.4 m) with a capacity of 1200 tons, and secondly in two seaweed incubators (20 m*20 m*1 m) and purified, and the final effluent after the final treatment process may undergo a post-treatment process and be sprayed (discharged) according to the existing sewage effluent water quality standards.

Such effluent water quality standards comprise biological oxygen demand (BOD, mg/L) of 30 or less; Chemical Oxygen Demand (COD, mg/L) of 50 or less; Total Organic Carbon (TOC, mg/L) of 3000 or less; Total Nitrogen (T-N, mg/L) of 60 or less; Total phosphorus (T-P, mg/L) of 8 or less; Suspended matter amount (SS, mg/L) of 30 or less; and Total coliform count (number/mL) of less than 3000.

In the microalgae incubator of the process step of the present disclosure, microalgae of 100 kg/200 ton filtration water/day may be harvested, wherein the microalgae may absorb nutrients and heavy metals of 84% of N; 77% of P; 94% of $Zn^{2+}$; 100% of $Cu^{2+}$ (up to 10 ppm); and 100% of $pb^{2+}$ (up to 5 ppm). In addition, 200 tons/day of filtered water excluding the harvested microalgae biomass may be continuously supplied to the marine algae incubator.

In the marine algae incubator, 204 kg/200 tons of filtered water/day of marine algae may be harvested, wherein the marine algae may absorb nutrients and heavy metals of approximately 16% of N (up to 84%), 23% of P (up to 31%), 27 to 66 ppm of $Zn^{2+}$, 16 to 38 ppm of $Cu^{2+}$ and 9 to 41 ppm of $pb^{2+}$. In addition, 200 ton/day of filtered water excluding harvested marine algae biomass may be sprayed and discharged.

The biomass of harvested microalgae and marine algae has productivity of 30.4 kg/day and $CO_2$ absorption of 54.7 kg/day through dry feed making, and the biochemical nutrients of the final produced feed may satisfy the conditions of more than 50% of protein, more than 20% of carbohydrate and 9% or less of lipid. Through such biomass convergence production system, it is possible to purify liquid fertilizer based on effluent water quality and economically produce algae biomass.

FIG. 4 shows a flow chart of a resource-circulation-type and eco-friendly livestock manure treatment method using algae biomass according to an embodiment of the present disclosure.

The resource resource-circulation-type and eco-friendly livestock manure treatment method using algae biomass of the present disclosure may comprise an algae selection step S100 of preparing algae capable of being cultured and proliferating as inoculum; a clean culture step S200 of culturing the selected algae in a culture medium in which a livestock liquid fertilizer is mixed with water to produce algal biomass, in an algal biomass production system; a feed material production step S300 of harvesting the algal biomass, followed by drying and pulverizing to obtain algal biomass powder; and a post-treatment step S400 of subjecting the culture medium remaining after harvesting the algal biomass in the clean culture step with water treatment, followed by spraying or discharging, but the present disclosure is not limited thereto.

FIG. 5 shows an algal biomass production system for treating resource-circulation-type and eco-friendly livestock manure using algae biomass according to an embodiment of the present disclosure.

The algal biomass production system may comprise, as a culture device used in the clean culture step of the resource-circulation-type and eco-friendly livestock manure treatment method using algal biomass, a controller 100 for controlling the culture environment; a medium preparation tank 200 for preparing a culture medium for culturing microalgae or marine algae; a first culture tank 300 for culturing microalgae by introducing the culture medium and microalgae as inoculum into; a first filtration tank 400 for filtering the microalgae and culture medium cultured in the first culture tank 300; a second culture tank 500 for culturing marine algae by introducing the culture medium obtained from the first filtration tank 400 and marine algae as inoculum into; and a second filtration tank 600 for filtering the marine algae and culture medium cultured in the second culture tank 500.

In the clean culture step, the controller 100 may store and analyze data that may be derived from the culture process, and control and optimize the culture environment. That is, the controller 100 may have a multipurpose water quality meter in each culture tank to measure temperature, pH, salinity, etc. to collect and analyze environmental information in real time through the control panel. In order to maintain the optimal culture temperature in the culture chamber, it is preferable for the controller to have a cooling device (not shown) and a warming device (not shown) to adjust the temperature.

In addition, an LED may be provided for effective culture of algae, and at this time, a 16-hour photoperiod and an 8-hour dark cycle may be set under LED light. Such LED light may be installed in a transparent tank to enable waterproofing and installed vertically in the culture tank.

The medium preparation tank 200 may prepare a custom liquid fertilizer suitable for the culture medium of microalgae or marine algae. Here, the custom liquid fertilizer may be prepared by properly mixing the livestock liquid fertilizer and water, preferably in a volume ratio of 1:9 to 9:1.

A flow meter may be used to sensor the amount of culture medium supplied from the medium preparation tank 200 to the first culture tank 300; the amount of culture medium supplied from the first culture tank 300 to the second culture tank 500; the amount of culture medium discharged from the second culture tank 500 to the outside, and adjust such amounts by using a submersible pump.

In the first culture tank 300, the culture medium mixed in the medium production tank 200 is supplied and microalgae are cultured, and, in the second culture tank 500, the culture solution is supplied from the first culture tank 300 and marine algae is cultured.

In addition, an agitator (not illustrated) is used to prevent the fine particles of the algae and culture solution from sinking in the first culture tank 300 and/or the second culture tank 500. At this time, the agitator may have a screw type, paddle type, propeller type or water turbine type, but the present disclosure is not limited thereto.

In addition, the culture tank may be selected from at least one of a raceway pond and a photo-bioreactor.

The microalgae in the first culture tank 300 are harvested by the harvesting method of the first filter tank 400, and the marine algae in the second culture tank 500 is harvested by the harvesting method of the second filter tank 600, which is an important process to be solved in the process of producing useful substances through mass cultivation of algae. Suitable harvesting methods depend on the species of algae and the use of useful substances to be obtained from the algae. The microalgae may be harvested by selecting at least one of filtration, sedimentation, flotation, centrifugation, and flocculation, but the present disclosure is not limited thereto.

MODE FOR INVENTION

Hereinafter, the present disclosure is described in detail by embodiments and experimental embodiments. However, the following embodiments and experimental embodiments only exemplify the present disclosure, and the content of the present disclosure is not limited to the following embodiments and experimental embodiments.

EMBODIMENT

>Embodiment 1> Selection of Experimental Strains and Preparation of Culture Medium The strain used in this example is *Spirulina* maxima (Cy-023), which was distributed from the Korea Microalgae Culture Center (Pukyoung National University, Pusan, Korea) and used in the experiment.

It was subcultured in a 5 L Erlenmeyer flask using Society of Toxicology (SOT) medium, which is a *Spirulina* medium, at an optimal culture temperature (26 to 30° C.) in a microalgae culture room.

In order to remove suspended matter in livestock manure, a culture medium for each experimental group was prepared as a pretreatment such that the ratio of liquid fertilizer (LF) and distilled water prepared by applying membrane treatment technology was 3:7 (LF 30%), 5:5 (LF 50%) and 7:3 (LF 70%), and only the carbon source ($NaHCO_3$) to the composition of the SOT medium widely used for *Spirulina* culture was added to the culture medium of each experimental group.

At this time, the control was prepared by adding carbon source ($NaHCO_3$), nitrogen source ($NaNO_3$) and phosphorus ($K_2HPO_4$) to the composition of the SOT medium, and the salt concentration of all experimental groups and the control was constantly adjusted to 13 psu by adding NaCl.

Table 1 below compares the compositions of the control SOT medium for culturing *Spirulina* maxima and the input liquid fertilizer.

TABLE 1

| | Component | | SOT (g/L) | LF (g/L) | Change rate (%) |
|---|---|---|---|---|---|
| 1 | Total Carbon | TC | 2.3996 | 0.00435 | −99.8 |
| 2 | Total Organic Carbon | TOC | — | 0.00423 | — |
| 3 | Inorganic Carbon | IOC | — | 0.00012 | — |
| 4 | Total Nitrogen | T-N | 0.41175 | 0.641 | 55.6 |
| 5 | Total Phosphorus | T-P | 0.0889 | 0.133 | 49.6 |
| 6 | Calcium | Ca | — | 0.112 | — |
| 7 | Copper | Cu | — | 0.0016 | — |
| 8 | Iron | Fe | 0.00201 | 0.0043 | 113.9 |
| 9 | Potassium | K | 0.673 | 0.000123 | −99.9 |
| 10 | Magnesium | Mg | 0.02 | 0.22 | 1000 |
| 11 | Sodium | Na | 6.6361 | 0.464 | −93.0 |
| 12 | Phosphorus | P | 0.0889 | 0.16 | 79.9 |
| 13 | Zinc | Zn | — | 0.0093 | — |
| 14 | Phenol | | — | 0.00005 | — |

In Table 1 above, the biochemical composition of the liquid fertilizer is 0.00435 g/L of total carbon, 0.00423 g/L of total organic carbon, 0.00012 g/L of inorganic carbon 0.641 g/L of total nitrogen, 0.133 g/L of total phosphorus, 0.112 g/L of calcium, 0.0016 g/L of copper, 0.0043 g/L of iron, 0.000123 g/L of potassium, 0.22 g/L of magnesium, 0.464 g/L of sodium, 0.16 g/L of phosphorus, 0.0093 g/L of zinc, and 0.00005 g/L of phenol.

<Embodiment 2> Searching for Conditions for Culturing 1 L Scale of Microalgae (Optimal Culture Conditions)

As the ratio of the liquid fertilizer and standard culture medium (v/v ratio) disclosed in Embodiment 1, LF 30%, LF 50% and LF 70% were set for the experimental groups and SOT was set as the control group. Culture studies were conducted twice for 21 days in a total of four 1 L transparent jars. The temperature (26±0.5° C.), photosynthesis, effective amount, photon flux density (PPFD) (94.9±0.5 μmol/m2 s/12:12 L:D cycles) and humidity (60±5%) were kept constant in the microalgae culture room.

Embodiment 3

1. Establishment of Conditions for Culturing 200 L Scale of Microalgae (Establishment of an Energy/Material Hybrid Harvesting System)

As the ratio of the liquid fertilizer and standard culture medium (v/v ratio) disclosed in Embodiment 1, LF 30%, LF 50% and LF 70% were set for the experimental groups and SOT was set as the control group. It was carried out for 30 days in a total of four 200 L photobioreactors developed by the present inventors.

On Day 30 of culture, the sample was filtered and harvested with a 10 μm Müller gauze using a height difference for 1 hour to secure *S. maxima* biomass. The harvest was stored frozen at −50° C. for 48 hours, and then freeze-dried using a freeze dryer (OPERON, KOREA).

The dry sample was crushed using a mortar and pestle, and the powdered sample was refrigerated at 4° C. under shade.

2. Measurement of the Culture Environment

The culture environment was analyzed by measuring a water temperature, salinity and pH using YSI 556-01 (Nist, USA) for 30 days while the culture was in progress. As a result of the culture environment analysis, the average water temperature was 27.94±1.89° C., the highest was 30.55±0.59° C., and the lowest was 26.50±0.12° C. Although maintained at the set temperature (28° C.), the water temperature showed a change up to 4.05±0.71° C. due to the daily irradiation amount and temperature difference.

The salinity showed an average of 13.56±0.55 psu, a maximum of 14.23±0.57 psu, and a minimum of 12.78±0.32 psu, and increased as the culture progressed. The pH showed an average of 10.30±0.15, a maximum of 10.52±0.02 and a minimum of 9.93±0.01.

3. Analysis of the Water Quality of the Culture Medium

2 L of each of the culture media of Day 0 and Day 30 was filtered with a 10 μm Müller gauze, and water quality analysis for effluent water quality standard items (i.e., BOD, COD, SS, T-N, T-P, Zn, Ph, Cu and total coliform count) was requested to the KOTITI Testing & Research Institute. The results are shown in Table 2 below.

TABLE 2

| Standard | | Control (SOT) | LF 30% | LF 50% | LF 70% | Effluent water quality standard |
|---|---|---|---|---|---|---|
| Biological Oxygen Demand (BOD) (mg/L) | Day 0 | 0.3 | 18 | 149 | 93 | <30 |
| | Day 30 | 10.5 | 9 | 42 | 34 | |
| Chemical Oxygen Demand (COD) (mg/L) | Day 0 | 2 | 308 | 412 | 443 | <50 |
| | Day 30 | 28 | 187 | 233 | 287 | |
| Total Nitrogen (T-N) (mg/L) | Day 0 | 473 | 187 | 282 | 370 | <60 |
| | Day 30 | 346 | 124 | 214 | 312 | |
| Total Phosphorus (T-P) (mg/L) | Day 0 | 85 | 46 | 58 | 93 | <8 |
| | Day 30 | 78 | 37 | 60 | 99 | |
| Suspended solids (SS) (mg/L) | Day 0 | 4 | 206 | 176 | 513 | <30 |
| | Day 30 | 39 | 49 | 86 | 160 | |
| Total coliform count (count/mL) | Day 0 | 110 | 150 | 2250 | 1950 | <3,000 |
| | Day 30 | 805 | 905 | 1735 | 2205 | |
| Copper (Cu) (mg/L) | Day 0 | 0.003 | 0.08 | 0.12 | 0.84 | <3 |
| | Day 30 | 0 | 0.05 | 0.06 | 0.16 | |
| Zinc (Zn) (mg/L) | Day 0 | 0.009 | 3.12 | 3.91 | 7.07 | <5 |
| | Day 30 | 0 | 0.58 | 0.31 | 0.73 | |

* SOT: standard control medium, Day 0: before culture, Day 30: after culture

* Effluent water quality standards are the effluent water quality standards of manure treatment facilities and livestock wastewater public treatment facilities of the Ministry of Environment.

As a result of comparing the water quality analysis results in Table 2, total nitrogen decreased in the control group and all experimental groups from Day 0 of culture to Day 30 of culture, and was measured as 346, 124, 214 and 312 mg/L, respectively. Total phosphorus decreased until Day 30 of culture in the control group and the LF 30% experimental group and increased in the LF 50% and LF 70% experimental groups.

On Day 30 of culture, 78, 37, 60 and 99 mg/L of total phosphorus were measured in the control and LF 30%, LF 50% and LF 70% experimental groups, respectively. On Day 30 of culture, the amount of suspended solids was greatly reduced to 49, 86 and 160 mg/L in the LF 30%, LF 50% and LF 70% experimental groups and increased to 39 mg/L in the control group.

It is judged that the remaining *S. maxima* biomass passed through the harvesting method of filtering with a 10 μm Müller gauze was measured as suspended matter. As a result of comparative analysis of BOD and COD values, the LF 50% experimental group showed the largest decrease rates of 72% and 43%, respectively, the LF 70% experimental group showed the decrease rates of 63% and 35%, respectively, and the LF 30% experimental group showed the decrease rates of 50% and 39%, respectively. In the control group, the BOD and COD values increased as the suspended solids ratio increased.

In addition, it was confirmed that the difference between the COD and BOD values was the greatest in the experimental group with LF 70%, which is because lignin, which is difficult to decompose to microorganisms, is oxidized during the COD measurement process such that the COD value is generally greater than the BOD value and biologically degradable, and the difference between the two values increases when there are many difficult forms of organic matter or substances toxic to microorganisms.

As a result of comparing total coliform counts before and after culture, after culture, the control group, LF 30% and LF 70% experimental groups showed increases to 805, 905, and 2205 counties/mL, respectively. Although the LF 50% experimental group showed a decrease to 1735 counties/mL, it was shown to be suitable for the effluent water quality standard of 3000 counts/mL.

The contents of copper and zinc, which are heavy metals, were 0, 0.05, 0.06, and 0.16 mg/L and 0, 0.58, 0.31, and 0.73 mg/L, respectively, for 30 days in the control group and all experimental groups (LF 30%, LF 50% and LF 70%), which were shown to be suitable for effluent water quality standards.

4. Calculation of a Liquid Fertilizer Concentration Suitable for Discharge

In order to explore the appropriate liquid fertilizer concentration for the items (i.e., COD, T-N, T-P and SS) that do not meet the effluent water quality standards for each experimental group in Item 3 (Analysis of the water quality of the culture medium) above, a standard curve was created based on the water quality analysis data of the present experiment. The calculated results are shown in Table 3 below.

TABLE 3

| Standard | Effluent Water quality standard | LF 6.2% | LF 7.7% | LF 14.4% | LF 17.6% | LF 30% | LF 50% | LF 70% |
|---|---|---|---|---|---|---|---|---|
| Chemical Oxygen Demand (COD) (mg/L) | <50 | 49.9 | 56 | 83.1 | 96.1 | 187 | 282 | 370 |
| Total Nitrogen (T-N) (mg/L) | <60 | 23.4 | 30 | 59.8 | 74.0 | 124 | 214 | 312 |
| Total Phosphorus (T-P) (mg/L) | <8 | 5.8 | 7.8 | 17.1 | 21.5 | 37 | 60 | 99 |
| Suspended solids (SS) (mg/L) | <30 | 4.6 | 7.9 | 22.7 | 29.8 | 49 | 86 | 160 |

* COD, y = 4.0514x + 24.822 (y: COD value, x: liquid fertilizer concentration)
* T-N, y = 4.443x − 4.1121 (y: T-N value, x: liquid fertilizer concentration)
* T-P, y = 1.3794x − 2.729 (y: T-P value, x: liquid fertilizer concentration)
* SS, y = 2.2084x − 9.0654 (y: SS value, x: liquid fertilizer concentration)

When culturing *S. maxima*, the ratio of culture water and liquid fertilizer suitable for each of the effluent water quality standards BOD, COD, T-N, T-P and SS was 30%, 6.2%, 14.4%, 7.7% and 17.6% or less, respectively, and suitable total coliform count, Cu and Zn were less than 70% (see Tables 2 and 3).

As a result, it was predicted that the culture medium prepared with the ratio of the liquid fertilizer of 6.2% or less in the culture water would be suitable for all effluent water quality standards. In the entire microalgae culture treatment process, the amount of available liquid fertilizer in manufacturing the culture medium at the ratio of 6.2%, as compared to the amount of approximately 1,613 tons, is 100 tons. When culturing microalgae with a high concentration of liquid fertilizer, it is judged that satisfying the effluent water quality standards must be accompanied by additional culturing of algae using the remaining culture medium after the completion of the culture.

5. Analysis of Biomass Components

On dried samples, analysis of the teed acceptance standard items, i.e., general ingredients (moisture, crude protein, crude fat, crude fiber, crude ash content), inorganic substances (phosphorus, zinc, copper) and heavy metals (lead, cadmium, arsenic, mercury, chromium, arsenic), was requested to the Korea Feed Technology Research Institute, and the results are shown in Table 4 below.

TABLE 4

| | Standard | Control (SOT) | LF 30% | LF 50% | LF 70% | Feed acceptance standards (ppm) |
|---|---|---|---|---|---|---|
| General Ingredients | Moisture (%) | 4.11 | 2.32 | 2.86 | 4.98 | — |
| | Crude protein (%) | 52.67 | 55.26 | 52.24 | 51.48 | — |
| | Crude fat (%) | 0.53 | 0.52 | 0.35 | 0.05 | — |
| | Crude fiber (%) | 0.54 | 1.16 | 2.03 | 1.46 | — |
| | Crude ash (%) | 15.63 | 13.06 | 15.36 | 17.72 | — |
| Minerals | Phosphorous (%) | 1.31 | 1.03 | 1.49 | 2.59 | — |
| | Zinc (%) | 23 | 1084 | 2432 | 3520 | Weaner pig: <2500, Feeder pig: 75 to 150 |
| | Copper (%) | 2 | 107 | 71 | 177 | 60 to 135 |
| Heavy metals | Lead (%) | 0 | 0 | 0 | 0 | 30 |
| | Cadmium (%) | 0.04 | 0.06 | 0.1 | 0.13 | 2.5 |
| | Arsenic (%) | 0 | 0 | 0 | 0 | 40 |
| | Mercury (%) | 0 | 0.004 | 0.0036 | 0.0049 | 1 |
| | Chromium (%) | 1.08 | 1.3 | 3.38 | 3.97 | 100 |
| | Fluoride (%) | 6.1 | 4.77 | 6.35 | 11.05 | 1000 |

* Feed acceptance standards are the standards and specifications of feed, etc. of the Ministry of Agriculture, Food and Rural Affairs.

As a result of comparing the analysis of the components in Table 4, samples with 178.8, 98.72, 70.12 and 65.29 g (dry cell weight) were obtained in the control, LF 30%, LF 50%, and LF 70% experimental groups, respectively.

As a result of the analysis of general components, the crude protein content was the highest at 55.26% in the LF 30% experimental group, followed by 52.67%, 52.24% and 51.48% in the control group, LF 50%, and LF 70%, respectively, and the moisture, crude fiber, and ash contents were 4.98%, 1.46% and 17.72%, respectively, relatively high in the 70% LF experimental group.

As a result of the analysis of minerals, the zinc and copper contents were significantly higher in the experimental groups than in the control group. The zinc contents of the LF 30% and LF 50% experimental groups were 1084 and 2432 ppm, which are not suitable for the feed standards for growing pigs but are suitable for the feed standards for weaner pigs. In the LF 70% experimental group, zinc and copper contents exceeded the permitted feed standard values and seemed to be unsuitable for being used as feed.

Among the heavy metals, lead and arsenic were not detected in the experimental and control groups, and cadmium, mercury, chromium, and fluorine were detected the most in the LF 70% experimental group, in the amounts of 0.13, 0.0049, 3.97, and 11.05 ppm, respectively, but the heavy metal contents of all experimental and control groups were found to be suitable for feed acceptance standards.

Embodiment 4

1. Selection of Experimental Strains and Preparation of Culture Medium

The strain used in the present experiment is *Ulva pertusa*, which was collected from the Sinyang port area in Goseong-ri, Seongsan-eup, Seogwipo-si, Jeju-do and used in the experiment. 100.8 g of $NaHCO_3$, 6 L of LF, and 252 g of NaCl were added to 15 L of distilled water to prepare 21 L of 15 psu culture medium, in accordance with the culture conditions of the LF 30% experimental group after culture specified in Item 3 of Example 3 (Analysis of the water quality of the culture medium). In addition, 21 L of culture medium was prepared by mixing Magma seawater (MS) with a salt concentration of 33 psu with distilled water, or MS with a salt concentration of 15 psu with distilled water at a ratio of 10:11, so as to use them as a positive control and a negative control, respectively.

2. Establishment of Conditions for Culturing 25 L Scale of Marine Algae (Establishment of Energy/Material Hybrid Harvesting System)

In the present experiment, the culture study was conducted for a total of 8 days in a total of four 25 L transparent jars. The temperature (28±0.5° C.) PPM (108.4±0.5 μmol/m2·s/12:12 cycles), and humidity (50±5%) were kept constant in the algae culture room.

Experimental groups were inoculated with 160 g and 200 g of *U. pertusa*, respectively, and each of the positive and negative control groups was inoculated with 160 g of *U. pertusa*. On Day 8 of culture, the biomass of *U. pertusa* was filtered and harvested with a 10 μm Müller gauze.

The harvest was stored frozen at −50° C. for 48 hours and then freeze-dried using a freeze dryer (OPERON, KOREA). The dried sample was crushed using a mortar and pestle, and the powdered sample was refrigerated at 4° C. under shade.

3. Analysis of the Water Quality of the Culture Medium

2 L each of the culture medium on Day 0 and Day 8 of culture was filtered with a 10 μm Müller gauze, and water quality analysis for the effluent water quality standard items (i.e., T-N and T-P) was requested to the KOTITI Testing & Research Institute. The results are shown in Table 5 below.

TABLE 5

| | MS 15 psu | | MS 33 psu | | LF 160 g | | LF 200 g | |
|---|---|---|---|---|---|---|---|---|
| | Total Nitrogen (T-N) | Total Phosphorous (T-P) | T-N | T-P | T-N | T-P | T-N | T-P |
| Day 0 | 0.7 | 0.073 | 1.1 | 0.156 | 138.8 | 36.74 | 138.8 | 36.744 |
| Day 8 | 1.9 | 0.070 | 2.6 | 0.134 | 121.6 | 31.39 | 123.0 | 24.024 |

* LF 160, y = −2. 15x + 138.8 (y: T-N value, x: days of culture)
* LF 160, y = −0.669x + 36.744 (y: T-P value, x: days of culture)
* LF 200, y = −1.975x + 138.8 (y: T-N value, x: days of culture)
* LF 200, y = −1.59x + 36.744 (y: T-P value, x: days of culture)

As a result of comparing the analysis of the water quality in Table 5, total nitrogen decreased from Day 0 of culture to Day 8 of culture and was measured as 121.6 mg/L in the LF 160 g experimental group and 123 mg/L in the LF 200 g experimental group. In the control group, it increased from Day 0 of culture to Day 8 of culture and was measured as 1.9 mg/L in the negative control MS 15 psu and 2.6 mg/L in the positive control MS 33 psu.

Total phosphorus decreased from Day 0 of culture to Day 8 of culture and was measured as 31.392 mg/L in the LF 160 g experimental group and 24.024 mg/L in the LF 200 g experimental group. In the control group, it decreased from Day 0 of culture to Day 8 of culture and was measured as 0.07 mg/L in the negative control MS 15 psu and 0.134 mg/L in the positive control MS 33 psu.

Based on the results of Table 5, a standard curve was created for each experimental group in order to select an appropriate incubation period and calculate the purification capacity according to the effluent water quality standards. The total nitrogen content of 60 mg/L, the effluent water quality standard, was met in the LF 160 g experimental group on Day 36.6 of culture and in the LF 200 g experimental group on Day 39.8 of culture. In addition, The total phosphorus content of 8 mg/L, the effluent water quality standard, was met in the LF 160 g experimental group on Day 42.9 of culture and in the LF 200 g experimental group on Day 18.0 of culture.

As a result, it is judged that, when culturing microalgae and marine algae is performed continuously, and optimal culture days for absorption of nutrients and heavy metals is accompanied, based on the previous experimental results, the livestock liquid fertilizer may be purified in accordance with the effluent water quality standards.

EXPERIMENT EXAMPLE

<Experiment Example 1> Comparison of Biomass Productivity According to Culture Conditions In order to measure the change in biomass, 20 mL of the culture medium containing *Spirulina* cells was sampled every 3 days and filtered (repeated three times) through a glass fiber filter paper (GF/C, 47 mm). After drying the filter paper in a dry oven (50° C.) for 24 hours, the weight before and after filtration was measured to calculate the biomass, and the results are shown in FIGS. 6 and 7.

In the 1 L scale culture experiment shown in FIG. 6, the initial biomass of *S. maxima* was 0.017±0.02 g/L, which was inoculated to the control group and all experimental groups. During the culture period, the maximum biomass yield in the control, LF 30%, LF 50% and LF 70% experimental groups was 1.10±0.05, 0.86±0.05, 0.72±0.07 and 0.68±0.003 g/L, respectively. It was confirmed that the cell growth rate was significantly high in the SOT medium-based control group on Day 21 of culture. In addition, the average biomass yield for 21 days of culture was measured as 0.60±0.37, 0.43±0.26, 0.39±0.22 and 0.35±0.19 g/L for each experimental group.

In the 200 L culture experiment shown in FIG. 7, the initial biomass of *S. maxima* was 0.14±0.01 g/L, which was inoculated to the control group and all experimental groups. During the culture period, the maximum biomass yield in the control, LF 30%, LF 50% and LF 70% experimental groups was 1.25±0.01, 0.76±0.02, 0.65±0.01 and 0.41±0.03 g/L, respectively. It was confirmed that the cell growth rate was significantly high in the SOT medium-based control group on Day 30 of culture. In addition, the average biomass yield for 21 days of culture was measured as 0.79±0.36, 0.54±0.19, 0.44±0.14 and 0.34±0.07 g/L for each experimental group.

As a result, it is considered that the turbidity according to the dilution factor of the liquid fertilizer affects the light transmission and inhibits the continuous growth of *S. maxima.*

<Experimental Example 2> Comparison of Nutrient Absorption According to Culture Conditions The ammonia ($NH_3$) content in the culture medium was measured using a Cedex Bio HT analyzer (Roche, Switzerland), a biochemical equipment for analyzing metabolites essential for a process for culturing animal cell and microorganisms. As a measurement method, 1 mL of microalgae culture medium was taken and centrifuged at 12,000 rpm for 1 minute, and metabolite analysis was performed using only the supernatant excluding cells. The results are shown in FIGS. 8 and 9.

In the 1 L scale culture experiment shown in FIG. 8, on Day 0 of culture, the ammonia content in the supernatant of LF 30%, LF 50% and LF 70% experimental groups and control group was measured as 22.70±0.07, 38.28±0.81, 53.78±0.24 and 0 mg/L, respectively, on average. On Day 3 of culture, the ammonia content decreased to 0 mg/L only in the supernatant of the LF 30% and LF 50% experimental groups. On Day 6 of tulrue, the ammonia content in the supernatant of the LF 70% experimental group was measured as 0 mg/L.

In the 200 L-scale experiment shown in FIG. 9, on Day 0 of culture, the ammonia content in the supernatant of LF 30%, LF 50% and LF 70% experimental groups and control group was measured as 13.56±0.10, 16.46±0.24, 35.66±1.10 and 0 mg/L, respectively, on average. On Day 6 of culture, the ammonia content decreased to 0 mg/L only in the supernatant of the LF 30% experimental group. On Day 9 of culture, the ammonia content was measured as 0 mg/L in the supernatant of the LF 50% and LF 70% experimental groups.

It was confirmed that ammonia was completely removed within each cultivation period regardless of the ammonia level in 1 L-scale culture and 200 L-scale culture. As such, it was confirmed that the ammonia nitrogen form did not appear as a toxic or inhibitory effect, and the growth of the experimental strain was not inhibited in a $NH_3$—N-concentration-dependent manner.

Embodiments about a resource-circulation-type and eco-friendly livestock manure treatment method using algal biomass, an algal biomass production system for treating resource-circulation-type and eco-friendly livestock manure using algal biomass, and use of the produced algal biomass according to an embodiment of the present disclosure were described above, but it is apparent that various modifications may be achieved without departing from the scope of the present disclosure.

Therefore, the scope of the present disclosure should not be limited to the embodiment(s) and should be determined by not only the following claims, but equivalents of the claims.

That is, it should be understood that the embodiments described above are not limitative, but only examples in all respects, the scope of the present disclosure is expressed by claims described below, not the detailed description, and it should be construed that all of changes and modifications achieved from the meanings and scope of claims and equivalent concept are included in the scope of the present disclosure.

INDUSTRIAL APPLICABILITY

The present disclosure relates to a resource-circulation-type and eco-friendly livestock manure treatment method using algal biomass, and a system for producing algal biomass used therein, which can prevent water pollution while allowing livestock liquid fertilizer to be treated on the basis of a biological process, and produce algal biomass.

The invention claimed is:

1. A resource-circulation-type and eco-friendly livestock manure treatment method using algal biomass, the method comprising:
   (a) an algae selection step of preparing algae capable of being cultured and proliferating as inoculum;
   (b) a clean culture step of culturing the selected algae in a culture medium in which a livestock liquid fertilizer is mixed with water to produce algal biomass, in an algal biomass production system;
   (c) a feed material production step of harvesting the algal biomass, followed by drying and pulverizing to obtain algal biomass powder; and
   (d) a post-treatment step of subjecting the culture medium remaining after harvesting the algal biomass in the clean culture step with water treatment, followed by spraying or discharging, wherein in step (b), the algae culture is performed by culturing microalgae, followed by culturing marine algae.

2. The method of claim 1, wherein the algae is at least one selected from the group consisting of microalgae and marine algae.

3. The method of claim 2, wherein the microalgae comprises at least one selected from the group consisting of *Spirulina* sp., *Chlorella* sp., *Scenedesmus* sp., *Chlorococcum* sp., *Chlamydomonas* sp., *Microcystis* sp. and *Euglena* sp.

4. An animal feed material containing algal biomass powder obtained by the resource-circulation-type and eco-friendly livestock manure treatment method using algal biomass according to claim 3.

5. The method of claim 2, wherein the marine algae comprises at least one selected from the group consisting of *Enteromorpha* sp., *Ulva* sp., *Saccharina* sp., *Garcilaria* sp. and *Sargassum* sp.

6. An animal feed material containing algal biomass powder obtained by the resource-circulation-type and eco-friendly livestock manure treatment method using algal biomass according to claim 5.

7. An animal feed material containing algal biomass powder obtained by the resource-circulation-type and eco-friendly livestock manure treatment method using algal biomass according to claim 2.

8. The method of claim 1, wherein in the culture medium of step (b), the liquid fertilizer and water are mixed in a volume ratio of 1:9 to 9:1.

9. An animal feed material containing algal biomass powder obtained by the resource-circulation-type and eco-friendly livestock manure treatment method using algal biomass according to claim 8.

10. The method of claim 1, wherein the harvesting of the algal biomass is performed by at least one of filtration, sedimentation, flotation, centrifugation and flocculation.

11. An animal feed material containing algal biomass powder obtained by the resource-circulation-type and eco-friendly livestock manure treatment method using algal biomass according to claim 10.

12. The method of claim 1, wherein the drying is performed by at least one of freeze drying, far-infrared ray drying, vacuum drying, hot air drying, spray drying, drum drying and natural drying.

13. An animal feed material containing algal biomass powder obtained by the resource-circulation-type and eco-friendly livestock manure treatment method using algal biomass according to claim 12.

14. The method of claim 1, wherein the water treatment is performed to meet effluent water quality standards of Biological Oxygen Demand (BOD, mg/L) of 30 or less; Chemical Oxygen Demand (COD, mg/L) of 50 or less; Total Organic Carbon (TOC, mg/L) of 3000 or less; Total Nitrogen (T-N, mg/L) of 60 or less; Total phosphorus (T-P, mg/L) of 8 or less; Suspended matter amount (SS, mg/L) of 30 or less; and Total Coliform Count (number/mL) of less than 3000.

15. The method of claim 1, wherein the method is performed using an algal biomass production system comprising:
   a controller for controlling culture environment;
   a medium preparation tank for preparing the culture medium for culturing the microalgae or the marine algae;
   a first culture tank for culturing the microalgae by introducing the culture medium and the microalgae as the inoculum into;
   a first filtration tank for filtering the microalgae and the culture medium cultured in the first culture tank;
   a second culture tank for culturing the marine algae by introducing the culture medium obtained from the first filtration tank and the marine algae as the inoculum into; and
   a second filtration tank for filtering the marine algae and the culture medium cultured in the second culture tank.

16. The method of claim 15, wherein the first culture tank and the second culture tank comprise at least one of a raceway pond and a photo-bioreactor.

17. The method of claim 15, wherein the first culture tank and the second culture tank comprise an agitator of at least one of a screw type, a paddle type, a propeller type and a water wheel type.

18. The method of claim 15, wherein the first culture tank and the second culture tank further comprise a heating device and a cooling device for maintaining an optimal culture temperature in the culture tank.

19. An animal feed material containing algal biomass powder obtained by the resource-circulation-type and eco-friendly livestock manure treatment method using algal biomass according to claim 1.

20. The animal feed material of claim 19, which is used as a raw material for feed additives or feed compositions.

* * * * *